United States Patent [19]

Bailey

[11] 4,257,426
[45] Mar. 24, 1981

[54] VACUUM ASSISTED ANTI-COAGULANT SYRINGE DEVICE FOR TAKING BLOOD SAMPLES

[75] Inventor: Donald L. Bailey, Thornton, Colo.

[73] Assignee: Marquest Medical Products, Inc., Englewood, Colo.

[21] Appl. No.: 50,970

[22] Filed: Jun. 22, 1979

[51] Int. Cl.³ .............................................. A61B 5/14
[52] U.S. Cl. ................................. 128/766; 73/425.6; 128/276; 128/218 P; 128/218 PA; 128/765
[58] Field of Search ............................... 128/763–766, 128/218 P, 218 PA, 218 R, 276, 278; 73/425.6

[56] References Cited

U.S. PATENT DOCUMENTS

| 2,102,785 | 12/1937 | Brooks | 128/763 X |
|---|---|---|---|
| 3,960,139 | 6/1976 | Bailey | 128/765 X |
| 3,965,889 | 6/1976 | Sachs | 128/764 |
| 4,085,749 | 4/1978 | Chambron | 128/276 X |
| 4,206,768 | 6/1980 | Bailey | 128/763 |

*Primary Examiner*—Kyle L. Howell
*Attorney, Agent, or Firm*—Gary M. Polumbus; Crandell & Polumbus

[57] ABSTRACT

A syringe device has a hollow tubular body that receives a resilient sealing member rotatably connected to a hollow plunger. A vacuum pump is connected through a flexible tube to the hollow plunger to thereby withdraw blood using the vacuum created. Once in the syringe body, blood is automatically exposed to an anticoagulant stored within the syringe body. The anticoagulant is in flake form and premanufactured from a heparin solution which is allowed to evaporate on a non-stick surface.

4 Claims, 8 Drawing Figures

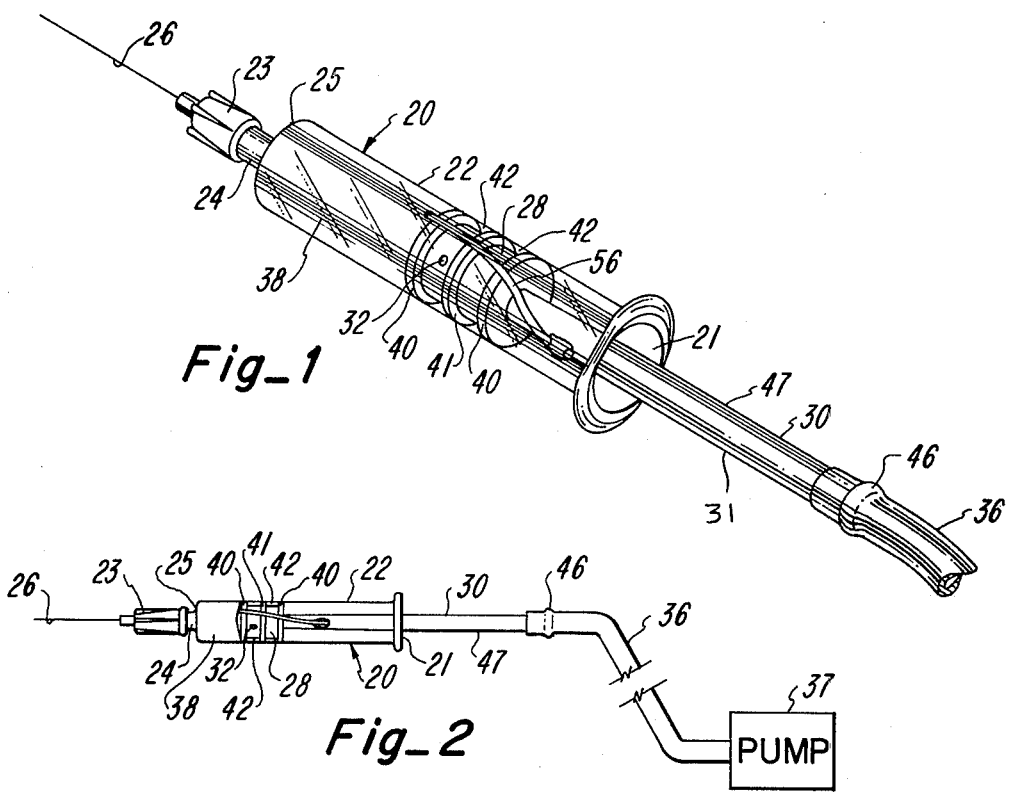
Fig_1
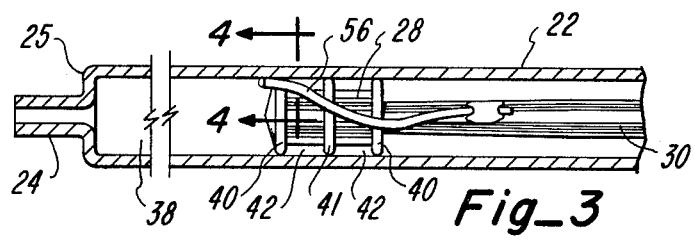
Fig_2
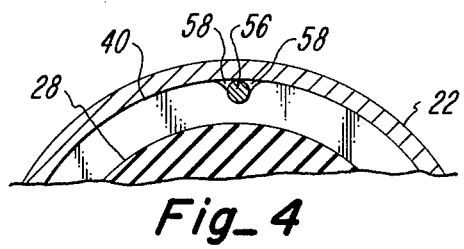
Fig_3
Fig_4
Fig_5
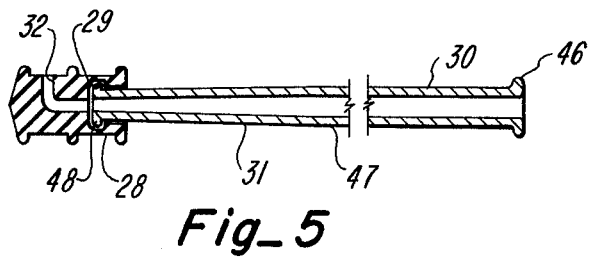

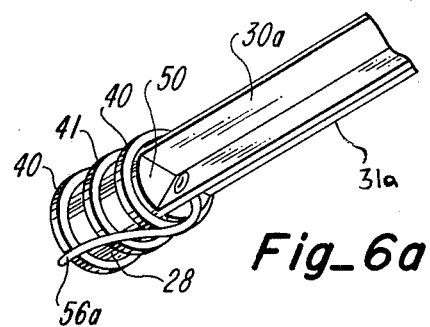
Fig_6a
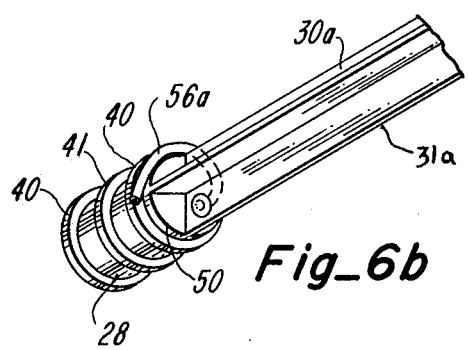
Fig_6b
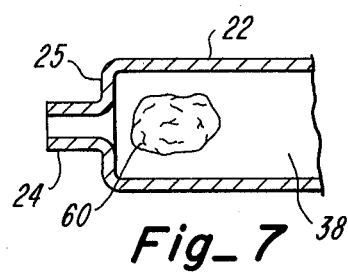
Fig_7
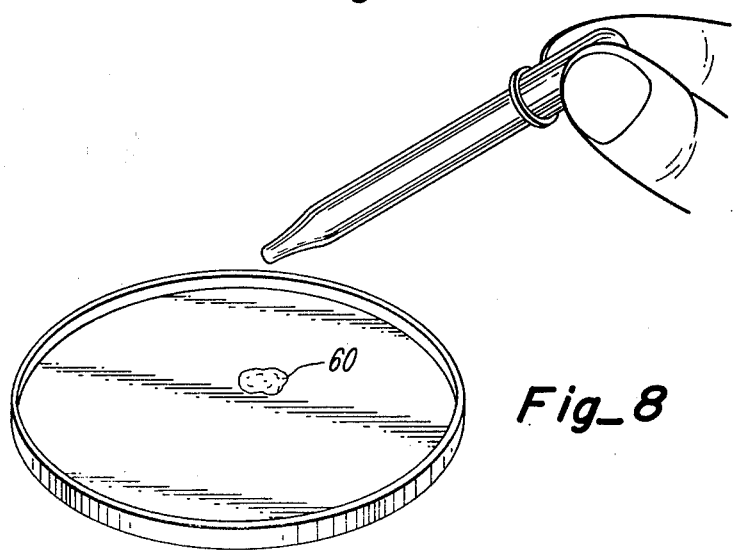
Fig_8

VACUUM ASSISTED ANTI-COAGULANT SYRINGE DEVICE FOR TAKING BLOOD SAMPLES

BACKGROUND OF THE INVENTION

1. Field of the Invention

This invention relates to syringes for collecting blood samples, and more particularly syringes of the type that are assisted in drawing blood by a vacuum in the interior of the syringe.

2. Description of the Prior Art

Syringe type devices are typically used for obtaining blood samples to perform a blood gas analysis. In these tests it is important that air and other materials contained in anti-coagulant solutions, such as water which is a diluent for the heparin, are not allowed to contaminate the blood and distort the results of the gas analysis. Several syringe devices have been developed to obtain contaminant free blood samples. Examples of such syringe devices are disclosed in my pending U.S. patent application for a Syringe Device With Means for Selectively Isolating a Blood Sample After Removal of Contaminates and Method of Using Same, Ser. No. 952,994, filed Oct. 20, 1978 and in U.S. Pat. Nos. 3,978,846 and 4,133,304 of which I am also the inventor.

However, not all individuals have a blood pressure which is high enough to fill the body of a syringe to a preselected volume necessary to conduct blood gas analysis. This is particularly true with small babies, especially premature babies, whose blood pressure is so low that it is difficult to get any flow whatsoever into a conventional syringe device. The newborn or premature baby problem is further complicated by the size of the arteries and veins and incumbent restrictions on the gauge of the needle that must be used to penetrate the artery or vein. The small dimensions, necessarily encountered, of the needle, impede any blood flow that might be expected.

In obtaining blood samples it is necessary to use an anti-coagulant to maintain the integrity of the blood sample. Typically, a dilute heparin solution of 1,000 units per milliliter in alcohol and water has been placed within the syringe body prior to use, which, after evaporation, leaves a deposit of heparin within the syringe body. This process takes a period of time, as long as an hour, and thus, undesirably extends the manufacturing time of the syringe when the syringe is provided with the dried heparin coating therein.

SUMMARY OF THE INVENTION

The syringe device of the present invention includes a main tubular body, the trailing end of which slidably receives a combination sealing member and hollow plunger, with the plunger geing rotatably connected to the sealing member. The plunger is also connected to a vacuum pump through a flexible hose. The leading end of the tubular body frictionally receives a hypodermic needle through a short extension portion thereof so that the needle extends longitudinally away from the main tubular body. The extension has a central bore through which blood received through the hypodermic needle can pass into the main tubular body of the syringe. Each end of the sealing member has an enlarged diameter circular lip, and an intermediate circular lip is disposed between the end lips, so that contact sufficient to create a seal exists between the lips on the sealing member and the syringe body. The sealing member has a lateral vent between the lip nearest the leading end of the sealing member and the intermediate lip, with the vent being communicative with the hollow interior of the plunger, the hose and vacuum pump. A flexible thread fixed to the plunger selectively crosses the lips and breaches the seal created by the sealing member to establish communication between the interior of the plunger and the interior of the tubular body via the lateral vent in the sealing member. Removal of the thread allows a seal to be restored so that a gas free blood sample can be isolated in the hollow tubular body.

Dry flake heparin is prepared from a sodium heparin solution for use in the syringe so that the heparin flakes can be placed in the syringe without unduly delaying the manufacturing process of the syringe. The sodium heparin solution, in the proper proportions, is dropped onto a non-stick flat surface, such as Teflon, and allowed to evaporate leaving a residue of dry flake heparin. The heparin flakes can be placed within the tubular body for immediate use, or stored for later use.

The principal object of the present invention is to provide a syringe device capable of drawing predetermined amounts of contaminant free blood from individuals with low blood pressure or from minute veins or arteries.

A related object of the present invention is to provide a syringe that can draw a preselected volume of contaminant free blood by use of a small gauge hypodermic needle.

It is a further object of the present invention to provide a new and improved anti-coagulant syringe device ready for immediate use in obtaining contaminant free blood samples.

Another object of the present invention is to provide a syringe device that can collect a blood sample free of gaseous contaminants from air and anti-coagulant diluent reactions with blood.

BRIEF DESCRIPTION OF THE DRAWINGS

FIG. 1 is a perspective view of the syringe portion of the present invention.

FIG. 2 is a plan view of the present invention with parts removed for clarity.

FIG. 3 is a fragmentary longitudinal section of the syringe portion of the invention with parts removed.

FIG. 4 is an enlarged fragmentary section taken along line 4—4 of FIG. 3.

FIG. 5 is a longitudinal section of with parts removed plunger.

FIG. 6a is a fragmentary perspective view of an alternative embodiment of the invention showing a flexible tube connected to the plunger and extending across the sealing member.

FIG. 6b is a view similar to FIG. 6a but showing the flexible tube wrapped onto the plunger and away from the sealing member.

FIG. 7 is a fragmentary longitudinal section of the syringe illustrating a heparin flake contained therein.

FIG. 8 is a perspective view of a flake of heparin formed on a non-stick surface.

DESCRIPTION OF THE PREFERRED EMBODIMENT

Referring to FIG. 1 of the drawings, a preferred form of the syringe 20 of the present invention includes a transparent or translucent main tubular body 22 of circular transverse section having an open trailing or rearward end 21 and a reduced diameter end fitting or neck 34 protruding axially from a leading or forward end wall 25 of the tubular body to which a hypodermic needle 26 is frictionally connected by a needle connector 23 in a hermetically sealed relation. The neck 24 is hollow and communicates with an interior chamber 38, generally defined by the space in the tubular body 22, the leading end wall 25 and a hollow plunger 30 which is received in the tubular body 22 through the open trailing end 21. A plunger body 31 is rotatably mounted within a resilient sealing member 28, and both the plunger body and sealing member, forming in combination the plunger, are received through the open trailing end 21 of the tubular body. The sealing member 28 is further adapted to slide along the interior surface of the main tubular body 22 in a sealed relationship therewith. The trailing end of the plunger body 31, which is at the opposite end of the plunger from the end where the sealing member 28 is mounted, is connected through a flexible hose 36 to a vacuum pump 37 (FIG. 2). A flexible thread 56 is permanently fixed to the plunger body 31 and is positioned to selectively cross the sealing member 28 in a manner and for purposes to be described in more detail later.

The elongated rigid tube-like body 31 terminates at its trailing end in an annular flange 46 of slightly larger diameter than that of the tube-like body 31 (FIG. 5). The intermediate tubular body 31 has a second annular flange 48 on its leading end adapted to be rotatably received in a recess 29 of a 'T' shaped cross-section in the trailing end of the sealing member 28. The plunger body, therefore, has an elongated dumbbell appearance. The annular flange 48 is rotatably received within the recess 29 of the sealing member 28 so as to provide for rotation of the plunger body 31 relative to the sealing member 28. Rotation of the plunger body 31 winds the thread 56 onto the body and pulls it away from the sealing member 28, thereby allowing a hermetic seal to be established between the sealing member and the interior surface of the tubular body 22. When the thread is allowed to extend across the sealing member, it breaches the seal and allows fluids to flow across the sealing member as will be explained more clearly later.

The plunger body 31 is connected to the thread 56 by glue or similar adhesive. (FIG. 3.) The thread 56 is of sufficient length to be extended across integral circular sealing lips 40 disposed at either end of the sealing member 28. A third circular sealing lip 41 is intermediate to sealing lips 40. The thread 56 is made of flexible material, such as nylon or cotton and has a diameter sufficient to form a breach or space 58 between the sealing lips 40 and 41 and the interior surface of the syringe body 22 when the thread 56 is extended across the sealing member 28.

As mentioned previously, the plunger body 31 is rotatably received within the sealing member 28. The annular flange 48 combines with the mating shape of the recess 29 to allow the sealing member to be moved axially within the syringe body 22 by the plunger body 31 to establish the volume of the blood sample desired. The circular mating configuration between the annular flange 48 and mating recess 29 permit rotational movement of the plunger body relative to the sealing member 28, a required capability for winding the thread 56 and removing the breach points 58. With the thread extended across the sealing member, it is readily apparent that as a sample of blood is taken, pre-existing gases within the chamber 38 are purged from the chamber through the breach points 58. Once the inflowing blood crosses the breach points 58, the thread is wound onto the plunger body, permitting the lips 40 and 41 to return to an undeformed shape, hermetically isolating a gas free blood sample in the chamber 38.

The sealing member 28 portion of the plunger is constructed of a material having elastic and resilient properties such as rubber. In its undeformed shape, the sealing member is generally cylindrical with the circular peripheral lips 40 at either end, and the intermediate circular lip 41 disposed therebetween. The lips 40 and 41 are of sufficient diameter to contact the interior surface of the syringe body 22 and form a sliding hermetic seal therewith. A pair of cylindrical void spaces 42, are defined between the body of the sealing member 28, the lips 40 and 41 and the internal surface of the main tubular body 22. The sealing member has a lateral vent 32 establishing fluid communication between the recess 29 and the void space 42 nearest the leading end 25 of the tubular body. It follows that fluid communication is provided with the hollow plunger 30 and the interior chamber 38 through the breach points 58.

The lateral vent 32, and the hollow plunger body 31, define a fluid passageway between the leading end void space 42 and the ambient environment (FIG. 5). Access of that passageway to the interior chamber 38 across the sealing member 28 is provided by the flexible thread 56, which indents the lips 40 and 41 to form the breach points 58 at each lip. The passageway so defined can be used to draw a vacuum on the interior chamber 38, thereby assisting the flow of blood into the chamber through the needle 26.

Though three circular lips 40 and 41 have been disclosed in regard to the sealing member 28, a pair of lips 40 will also perform certain aspects of the present invention as already described in my copending application Ser. No. 952,994 Syringe Device with Means for Selectively Isolating a Blood Sample After Removal of Contaminants and Method of Using Same. The additional lip increases the frictional forces between the sealing member 28 and the interior surface of the main tubular body 22 by increasing the contact area therebetween. This becomes important as a vacuum is drawn in the interior chamber 38.

The flexible hose 36, which may be rubber, latex or the like, is adapted to flexibley fit over the annular flange 46 of the plunger body 31 and from there connect to the vacuum pump 37 (FIG. 2). The vacuum pump 37 has specifications such that it is capable of creating a vacuum in the interior chamber 38 of the tubular body of between 100 and 150 millimeters of mercury. The tight fit of the three sealing lips 40 and 41 prevent the vacuum in the chamber 38 from pulling the sealing member 28 and the connected plunger body 31 axially along the tubular body 22. In this manner, the preselected volume of chamber 38 is established by manually moving the sealing member 28 by means of the plunger along the interior surface. Once selected, this volume will not be altered as vacuum is drawn in the interior chamber 38. From the foregoing, it can be seen that as vacuum is drawn by the pump 37, pressure is lowered in the interior chamber 38, encouraging blood to flow from an individual's blood stream through the needle 26 into the chamber 38.

This feature of the present invention is particularly important in using the syringe device 20 of the type disclosed with individuals having low blood pressure or with extremely small infants having small veins and arteries. The main advantage of the invention lies in the fact that once the sealing member 28 is set to a preselected position along the interior of the syringe body 22, a gas free blood sample can be collected regardless of the blood pressure of the individual from whom the sample is sought.

Additionally, a very small gauge needle, smaller than needles typically used in hospitals and health related organizations throughout this country, can be used routinely with the vacuum assist. The smaller gauge needle presents greater resistance to fluid flow than does the large gauge needle and therefore the use of a vacuum assist permits the use of smaller needles than would otherwise be possible.

The hypodermic needle 26 is connected to the syringe 22 at the end fitting 24 in a manner well known in the art. The entire syringe 20 and the parts thereof are made of presterilized glass materials which can be prepackaged and discarded after use, a procedure universally adopted in the health care industry.

In an alternative embodiment of the present invention, the thread 56 is replaced by a relatively short flexible and resilient tube 56a, which can be made of polyethylene (FIG. 6a). In this embodiment, two or three sealing lips may be used and vacuum assist though the hose 36 is not used. This is partially because a smaller diameter plunger body 31 must be used to fit the hose 36, and the tube 56a, which has a relatively small diameter itself, cannot be readily fixed to it. The interior chamber 38 is filled with blood by the individual's blood pressure alone. On low blood pressure individuals, the sealing member 28 is set at a relatively low volume setting such as 0.1 to 0.2 CC, and blood is allowed to flow into the chamber. After the low volume chamber is completely full of blood and blood begins to pass through the breach points 58, the breach points are eliminated by winding the tube 56a onto the plunger body 31a (FIG. 6b), and the plunger 30a is then pulled out relative to the tubular body 22 enlarging the size of the chamber 38 and simultaneously withdrawing blood until the proper volume is achieved.

The tube 56a of the alternative embodiment is tied to the plunger body 31, preferably near a disc 50 attached to the plunger adjacent to the connection location of the plunger body to the sealing member 28. The tube 56a then can be extended across the sealing member 28 in a manner as described with the thread 56. It has been found that one desirable feature of the tube 56a is that it spreads the forces between the sealing member 28 and the interior of the syringe body 22 over a greater area, whereby permanent deformation of the sealing member 28 is less likely to occur. This becomes a significant advantage when syringes 20 are stored for extended periods of time.

It is of course necessary to make sure that the blood sample taken does not coagulate and ruin the results of analyses taken on the sample. Typically an anti-coagulant, such as heparin, is utilized to coat the interior chamber 38 of the tubular body. A solution of anti-coagulant, in the past, has been placed in the chamber and allowed to evaporate leaving a dried anti-coagulant precipitate in the interior chamber 38. The heparin solution is typically very dilute, the heparin concentration being 1,000 units per milliliter in a diluent of alcohol and water.

Part of the present invention relates to pre-preparation of a dry flake of heparin 60 through a new and unique process and placing it in a dried state in the interior chamber 38 so that any blood received is immediately exposed to the heparin. It has been found that a solution of water and sodium heparin can be evaporated on a flat non-stick surface, such as Teflon, leaving a dry flake 60 FIG. 8) of heparin. Specifically, it has been found that a solution formed from a concentration of 3,000 or more units of sodium heparin per milliliter of water achieves the desired results. After formed, 20 to 60 microliters of that solution are allowed to evaporate leaving a dry residue having a concentration of 60 to 180 units of heparin.

The flake so produced has obvious advantages over prior methods due to the fact that the heparin flake 60 can be stored along with the tubular body 22 for immediate use of the syringe 20 (FIG. 7.) or the heparin flake can be produced prior to the syringe, and merely dropped in the syringe prior to storage. Prior methods were limited by a waiting period for the production of dried heparin in the syringe body.

OPERATION

After the heparin flake 60 has been placed in the body 22 of the syringe, the thread 56 is extended completely across the sealing member 28, slightly indenting all lips 40 and 41 and forming breach points 58. The plunger body 31, sealing member 28 and thread 56 are slidably inserted into the syringe body 22 through the open circular end 21 of the syringe 20. The plunger body 31 is used to position the sealing member 28 at a point along the tubular body 22 corresponding to the volume of blood sample desired. Typically, syringe bodies 22, are calibrated in volummetric units in order to facilitate this purpose.

The hypodermic needle 26 is frictionally connected to the neck 24 and is inserted into the artery of the donor patient where the blood pressure will normally force the blood through the needle 26 into the interior chamber 38 of the syringe body 22. The individual taking the sample should orient the syringe so that the breach 58 in the seal lip 40 nearest the needle 26 is disposed so as to be at the furthest distance possible from the rising level of the blood as it enters the interior chamber 38. The sealing member 28 thus acts as a dam and the breach created by the thread 56 or polyurethane tube 56a serves as a vent for air and gases which were pre-existant in the body 22 or were created by reaction of the blood with the anti-coagulant flake 60. Ultimately, after the interior chamber 38 is filled with blood, the breach 58 serves as a spillway through which the blood can pass into the void space 42. It will be appreciated that as the blood fills the interior chamber, the chamber is purged of all gaseous materials that might contaminate the blood sample.

As the blood reaches the point 58 and crosses the first lip 40 into the void space 42, the plunger body 31 is rotated so as to wind the thread 56 or tube 56a about the plunger body 31a thus pulling the thread past the forwardmost sealing lip 40 establishing a complete seal at that location. Continued rotation of the plunger body 31 will pull the thread 56 or tube 56a past the remaining lip or lips 40 and 41 of the sealing member 28 thus establishing a complete seal at that location to trap the blood that flowed into the void space 42 and thus prevent leakage of any blood from the syringe 20.

The present invention is adapted for use with individuals having extremely low blood pressures. Absent vacuum assist, the procedure described with reference to use of the polyethylene tube 56a should be used.

When vacuum assist is available, the hose 36 is attached to the flange 46 of the plunger body 31. Actuation of the vacuum pump 37 creates a vacuum of between 100 and 150 milliliters of mercury in the interior chamber 38 of the syringe 20. Blood is thus drawn into the interior chamber 38 when it might not ordinarily flow. This procedure is also particularly useful in treating infants, where a very small gauge needle, smaller than normally used in hospitals and medical facilities, can be utilized to enter the very small veins or arteries of a baby. Normally, such a small gauged needle constricts blood flow and would not permit the interior chamber 38 to be filled by even normal blood pressure.

It will be understood that changes may be made in details of construction, arrangement and operations without departing from the spirit of the invention, especially as defined in the appended claims.

What I claim is:

1. A syringe device of the type used for drawing blood samples, the device having a generally tubular body with an open rearward end and a forward end adapted to receive a hypodermic needle in a manner to establish fluid communication between said needle and the interior of said tubular body, a plunger adapted to be slidably positioned within said tubular body to define a preselected volume within the tubular body, said plunger including a hollow elongated body, a resilient sealing member rotatably connected to the elongated body having a vent therethrough in communication with the hollow interior of said plunger body, and seal interruption means allowing communication between the vent of said sealing member and the interior of said tubular body forwardly of said sealing member, a flexible hose operably connected to said elongated body to establish fluid communication between the interior of said elongated body and the flexible hose, and vacuum pump means operatively connected to said hose whereby pressure can be lowered within the interior of said tubular body forwardly of said sealing member to thereby draw blood into the syringe when said seal interruption means is operative to allow communication between the vacuum pump means and the interior of said tubular body forwardly of said sealing member.

2. The invention defined in claim 1 wherein the interior of said tubular body has contained therein a dry flake of heparin.

3. The invention defined in claim 1 wherein said sealing member is of generally cylindrical shape having a an forward end circumferential lip, a rearward end circumferential lip, and an intermediate circumferential lip between said end lips, said lips adapted to fully contact said tubular body's interior surface.

4. The invention defined in claim 3 wherein said transverse vent is located between the forward end lip and the intermediate lip.

* * * * *